US006436344B1

(12) United States Patent
Miekka et al.

(10) Patent No.: US 6,436,344 B1
(45) Date of Patent: Aug. 20, 2002

(54) METHOD OF INACTIVATING PATHOGENS

(75) Inventors: Shirley I. Miekka, Gaithersburg, MD (US); William H. Drohan, Springfield, VA (US); Herbert Baumann, Jarfalla (SE); Ingrid Drevin, Uppsala (SE); Jean-Luc Maloisel, Enebyberg (SE)

(73) Assignees: American National Red Cross, Falls Church, VA (US); Amersham Pharmacia Biotech AB, Uppsala (SE)

( * ) Notice: Subject to any disclaimer, the term of this patent is extended or adjusted under 35 U.S.C. 154(b) by 0 days.

(21) Appl. No.: 09/431,922

(22) Filed: Nov. 2, 1999

(51) Int. Cl.$^7$ .............................. A01N 1/00; C23F 11/10; A61K 31/11
(52) U.S. Cl. .............................. 422/36; 422/17; 422/28; 422/37; 514/693
(58) Field of Search .............................. 422/17, 28, 29, 422/36, 37; 514/693

(56) References Cited

U.S. PATENT DOCUMENTS

| | | | |
|---|---|---|---|
| 3,903,150 A | 9/1975 | Reinhold | 260/534 |
| 4,481,189 A | 11/1984 | Prince | 424/101 |
| 4,540,573 A | 9/1985 | Neurath et al. | 424/85 |
| 4,820,805 A | * 4/1989 | Neurath et al. | 530/410 |
| 4,841,023 A | 6/1989 | Horowitz | 530/351 |
| 4,909,940 A | 3/1990 | Horowitz et al. | 210/634 |
| 5,041,442 A | * 8/1991 | Romero et al. | 514/249 |
| 5,055,485 A | 10/1991 | Geacintov et al. | 514/449 |

FOREIGN PATENT DOCUMENTS

| | | |
|---|---|---|
| EP | 402-646 A1 * | 5/1990 |
| GB | 929034 | 6/1963 |
| WO | WO/9747200 | 12/1997 |

OTHER PUBLICATIONS

J. Steven Jacobsen and M. Zafri Humayun, Mechanisms of Mutagenesis by the Vinyl Chloride Metabolite Chloroacetaldehyde. Biochemistry, vol. 29, Nov. 2, 1990, pp. 496–504.*
S. Premaratne et al, "Identification of DNA Adducts at Specific Locations by Sequencing Techniques", *Int. J. Biochem*, vol. 25, No. 11, pp. 1669–1672 (1993) XP–00989542.
Premaratne, "Identification of DNA Adducts at Specific Locations by Sequencing Techniques", *Int. J. Biochem*, vol. 25, No. 11, pp. 1669–1672 (1993).
Borys, "The Induction of Adaptive Responsle to Alkylating Agents in *Escherichia coli* Reduces the Frequency of Specific C—T Mutations in Chloroacetaldehyde–Treated M13 *glyU*Phage", *Mutagenesis*, vol. 9, No. 5, pp. 407–410 (1994).
Jacobsen, "Mechanisms of Mutagenesis by the Vinyl Chloride Metabolite Chloroacetaldehyde, Effect of Gene-Targeted in Vitro Adduction of M13 DNA on DNA Template Activity in Vivo and in Vitro", *Biochemistry*, vol. 29, No. 2, pp. 496–504 (1990).

* cited by examiner

Primary Examiner—Robert J. Warden, Sr.
Assistant Examiner—Imad Soubra
(74) Attorney, Agent, or Firm—Burns, Doane, Swecker & Mathis, L.L.P.

(57) ABSTRACT

The present invention introduces a class of compounds, 2-substituted carbonyl compounds, that are useful as disinfecting agents, and particularly useful in methods for the disinfection of biological fluids. Members of the class of compounds have been found to possess pathogen inactivating properties against a variety of pathogens. The compounds and methods disclosed herein are useful for disinfecting biological fluids such as blood and blood fractions, among others.

15 Claims, 5 Drawing Sheets

Preservation of Coagulation Factor IX activity with CAA treatment for 0 - 20 hr at 37°C Figure 1. Concentration Dependence of PPV Inactivation by Iodoacetaldehyde in Buffer and 5% IgG Figure 2. Concentration Dependence of PPV Inactivation by Chloroacetaldehyde in Buffer and 2.5% IgG Figure 3. Kinetics of PPV Inactivation by 2mM Chloroacetaldehyde in Buffer and 2.5% IgG Figure 4. Preservation of Coagulation Factor VIII activity with 0 – 12.8 mM CAA treatment at 37°C Figure 5. Preservation of Coagulation Factor IX activity with CAA treatment for 0 - 20 hr at 37°C

METHOD OF INACTIVATING PATHOGENS

FIELD OF THE INVENTION

The present invention provides a class of compounds, certain 2-substituted carbonyl compounds (2-substituted aldehydes, ketones and carboxylic acid esters), that are capable of killing and/or inactivating pathogens. Members of this class of compounds disinfect biological fluids containing clinically significant biological materials such as proteins and the like without substantial deleterious effect on those materials. It is further contemplated that the disinfecting agents and formulations of the present invention might be used to treat infected multi-cellular organisms, including mammals.

BACKGROUND OF THE INVENTION

Previously it has been suggested to disinfect air, water, and other materials by bringing the material in contact with various forms of iodine. It has been reported that various biological materials can be disinfected by contacting those materials with iodine-loaded support matrices, such as polyvinyl pyrrolidone. That kind of disinfection has been carried out both as a therapeutic treatment regimen, for instance disinfection of wounds, and for disinfecting various solutions, in particular aqueous solutions such as drinking water, protein solutions, etc. See, e.g., U.S. Pat Nos. 3,817,816; 3,817,860; 4,010,259; 4,190,529; 4,420,590; 4,594,392; 5,639,452; WO 9516511; WO 9748422; WO 9748482; and Hatch G. L., Ind. Eng. Chem. Prod. Res. Dev. 20(2) (1981) 382–5.

Recently, it was discovered that a particularly advantageous effect could be achieved with a solution comprising an effluent taken off an iodinated ion exchange matrix material. The effluent mixture had several surprising advantages: it inactivated a wide range of potent and hardy pathogens without substantial deleterious effect on clinically significant substances such as proteins. Thus, for example, the effluent mixture provided an effective means for disinfecting blood and blood-derived products; thereby affording a greater level of safety in the use of those essential materials. See U.S. patent application Ser. No. 09/159,460.

One of the drawbacks of iodine-loaded support matrices is that they are cumbersome to manufacture, and present uncertainty in application. For example, many proteins, particularly acidic proteins such as Factor IX and albumin, bind to the iodine-loaded matrices. Such protein binding impairs the efficiency and effectiveness of the process. Likewise, protein binding can result in molecular modification of the protein, thereby affecting its biological activity.

Another drawback is that many iodinated matrices release iodide ions and certain oxidizing forms of iodine. Exposure of labile proteins and other clinically significant biological materials to such potent oxidizers must be limited; and so the oxidizing substances must ultimately be removed from the disinfecting mixture. Thus, biological fluids treated with such matrices must be subjected to a laborious and expensive capture step during or shortly after treatment to remove the more noxious forms of iodine.

Moreover, since the actual active agent in the effluent mixtures was not known, those systems presented uncertainties in determining the presence, concentration, efficacy, and stability of the anti-pathogenic agent in any given mixture; and further presented complications in effectively separating the anti-pathogenic agent from otherwise noxious forms of iodine.

Various species of iodine have been suggested as the active agent(s) in those systems. For example, it has been suggested that an active anti-pathogenic agent might be iodine or iodide, per se ($I_2$, $I^-$, or $I_3^-$); or other forms of iodine that form in aqueous media (e.g., HOI, OI$^-$). See, e.g., Hatch G. L., Ind. Eng. Chem. Prod. Res. Dev. 20(2) (1981) 382–5. However, none of those species has been shown to possess the unique features of, for example, the effluent of iodinated ion exchange media. Moreover, nothing in the art has established that those unique features are, in fact, attributable to a singular active agent or class of active agents.

Certain haloacetaldehydes have been synthesized and identified as having some potential clinical significance. For example, trichloroacetaldehyde, both as such and in proforms, has been reported to have medicinal use in liniments and as a sedative/hypnotic or anesthetic. Windholtz et al., THE MERCK Index, $10^{th}$ edition, p. 288 (Merck & Co., Rahway, N.J., USA (1983)); and Pharmaceutical Substances—Syntheses, Patents, Applications, pp 392–93 (Kleeman et al. eds., $3^{rd}$ edition, Thieme Stuttgart, New York (1999)). Trichloroacetaldehyde has also been used in pediatric medicine and dentistry (e.g., Smith, Science, p. 359 (Oct. 19, 1990); Drug Information, p. 937 (McEvoy, ed., American Hospital Formulary Service, American Society of Hospital Pharmacists, Bethesda, Md., USA, (1985)). Chloroacetaldehyde, a metabolite of vinyl chloride, has been implicated as a potential carcinogen and mutagen. See, e.g., Matsuda, T. et al, Carcinogenesis, 10, pp 2389–94 (Oct. 16, 1995); and Jacobsen J. S. et al., Genetics, 121 (2), pp 213–22 (February 1989). However, such materials have not heretofore been shown to be useful in disinfecting various kinds of material.

There is a need for improved compositions and formulations for disinfecting biological fluids and systems. For example, it would be profoundly advantageous to identify, isolate, and synthesize or otherwise more conveniently manufacture one or more discrete chemical agents that mimic the disinfectant capabilities of the effluent mixtures from iodinated ion exchange matrixes. Such advances will enable detection and quantitation of the active agent, which, in turn, will facilitate the preparation of dose-response curves, and efficacy and toxicity studies. The identification of the active agent will further improve the utility of such agents, and thereby improve public health. That is, the identification and further study of those active anti-pathogenic agents will facilitate more reliable and predictable disinfection of biological fluids, such as blood and blood products, and will thereby enhance the safety of clinically significant products and procedures employing those agents.

SUMMARY OF THE INVENTION

The present invention presents a class of 2-substituted carbonyl compounds that have pathogen inactivating capabilities. The compounds of the present invention can be formulated into storage stable compositions that are useful for, among other things, disinfecting biological fluids and other materials of biological or non-biological origin. The present invention further affords methods for disinfecting materials, including biological fluids and the like, without concomitant deleterious destruction of labile proteins or other biological materials of clinical significance.

A particular advantage of the compounds of the present invention is that these compounds can be formulated into well-defined compositions comprising a single well-defined active agent. Those compositions retain pathogen inactivating potential, and can be used in the presence of biological materials and clinically significant constituents. The compositions of the present invention can be conveniently manufactured and analyzed for, e.g., concentration, anti-pathogenic potency, efficacy, and storage stability. Thus, the compositions can be effectively standardized, and reliably compounded, packaged, and stored for subsequent use. By resort to a single-agent composition it also more likely that the use of these compounds will result in fewer deleterious reactions or by-products.

It is contemplated that the compounds of the present invention will be useful not only in disinfecting biological fluids and other biological material in vitro, but also as an in vivo or ex vivo therapeutic for treating or preventing infection in animals, including humans.

As used herein, and unless stated otherwise, the term "pathogen" includes viruses, bacteria, fungi, prions, prion related proteins, and other micro-organisms capable of exerting pathogenic effects in multi-cellular organisms. Thus, the use of the term "pathogen" contemplates micro-organisms capable of causing disease in mammals, including humans.

The term "pathogen-inactivating-effective amount" of an active agent for a pathogen present in a material means sufficient quantity or concentration as to reduce or maintain the level of pathogen in the material. The reduction is preferably to a non-pathogenic level. See also below.

The term "blood products" includes blood fractions and blood extracts such as plasma and blood derived products such as clotting factors, red cells, platelets, white cells, immunoglobulins, serum albumin and the like.

The term "biological fluid" refers to liquid mixtures containing one or more bioorganic compounds, e.g. proteins, carbohydrates, nucleic acids, lipids, hormones, amino acids etc, and/or one or more clinically significant constituents and/or pharmacologically active components. Bioorganic compounds may be of clinical significance and/or have pharmacological activity. A biological fluid might be a solution, liquid mixture, suspension, or a paste. The term further includes whole fluids (such as blood), as well as fractions, extracts, dialyzates, effluents, and other products of chemical, chromatographic, etc. separations. Thus, the term includes blood, blood fractions, blood extracts, blood plasma, protoplasm, milk, urine, semen, saliva, plant extracts, reaction products derived from vaccine production, cell culture supernatants, and other fluids, of either natural or synthetic origin (e.g., recombinant or transgenic); and various isolates, effluents, and extracts taken therefrom.

The term "materials of clinical significance" or "clinically significant constituents" refers to desired components, for instance bioorganic compounds and/or salts that are physiological active and/or physiologically acceptable, or materials having clinical or therapeutic activity, either as an agonist or antagonist, that may be present in biological fluids or derived of biological origin, whether natural, transgenic, or recombinant. The term includes pharmacologically active or useful proteins, polysaccharides, lipids, nucleic acids, and hormones.

The term "protein" refers to compounds comprised of one or more chains of amino acids connected by peptide linkages; and includes compounds containing any such fundamental peptide structure, e.g., oligopeptides and polypeptides, as well as oligo- and polypeptides covalently linked to matrices or polymeric supports. Protein mixtures include: liquid mixtures, pastes, or solutions of: albumin of various kinds (e.g. serum albumin); proteases; protease inhibitors; clotting factors such as fibrinogen, Factor VII, Factor VIII, and Factor IX; protein C; immunoglobulins, particularly IgG, including hyperimmune Igs; monoclonal antibodies, and growth factors. Other proteins of interest are lactoperoxidase and lactoferrin.

The term "disinfect" means to remove, kill, destroy, or otherwise render non-pathogenic a pathogenic component. Likewise, the term "pathogen inactivation" or "pathogen inactivating" means killing, destroying, or otherwise rendering non-pathogenic a pathogenic component of an otherwise pathogenic species. To render non-pathogenic means to impair a vital function of the pathogen or merely reduce it in number or concentration such that a host's immune system can otherwise dispose of it. Examples of pathogenic components are virus, bacterium, fungus, other pathogenic microorganisms, or other pathogenic species such as the infective agent for transmissible spongiform encephalopathies, e.g., prion, prion-related proteins ("PRP"), and the like.

The term "biological system" means multi-cellular organisms, and includes mammals.

As used herein, "materials" to be disinfected include inorganic and organic material, such as biological fluids, bioorganic molecules, clinically significant constituents, surfaces contaminated or suspected of being contaminated by pathogens, water, air, etc. In a broad sense the term also includes biological systems, for instance cell cultures and multi-cellular organisms such as animals potentially infected with the various pathogens or which are at risk of becoming infected with pathogens.

Unless stated otherwise, all quantities or concentrations expressed as a percentage (%) are percent by weight.

DETAILED DESCRIPTION OF THE INVENTION

The present invention introduces a discrete class of compounds not heretofore recognized to comprise compounds having pathogen inactivation as a common utility. The class of compounds is certain 2-substituted carbonyl compounds. The compounds can be effectively formulated into pharmaceutical compositions; and those compositions can be used in methods for disinfecting biological fluids. The compounds and compositions can be effectively employed in the presence of proteins and other clinically significant constituents, without imparting substantial deleterious effect. That is, mixtures containing clinically significant constituents can be treated with the compounds and compositions of the present invention, and the clinically signifi- cant constituents can be recovered without substantial loss of biological activity.

The 2-substituent (X) is a group that is able to behave as a leaving group in an aqueous nucleophilic substitution reaction, for instance in th pH-range 1–10. The most effective such leaving groups are weak bases, i.e. bases that have a $pK_b>8$ such as >9 (measured at 25° C. in dilute aqueous solutions). Preferably the leaving group is a halogen, and more preferably either chlorine or iodine. Iodine is the most preferred for the inactivation of hardy viruses. Members of the class of compounds of the present invention can be compounded into formulations or pharmaceutical compositions useful in disinfecting biological fluids. The compounds and formulations of the present invention are useful in methods for disinfecting biological fluids.

The carbon atom in position 2 may also carry other groups, such as lower alkyl ($C_{1-5}$) and the like. See for instance formula I below.

The preferred 2-substituted carbonyl compounds have at most one X-substituent at a 2-carbon atom.

The preferred pathogen inactivating compounds used in the present invention are selected from compounds comprising the structure (Formula I):

$$X—CR'R"—C(=O)O_m—R''' \qquad (I)$$

in which:
  m is an integer 0 or 1;
  X is a leaving group as discussed above enabling a nucleophilic substitution reaction in aqueous media at the 2-carbon in the compound of formula (I). Examplary groups X are halo, such as fluoro, chloro, bromo and iodo; sulphonates ($R_+—SO_3—$), such as tosylate and mesitylate; carboxylates (R—CO—O—). R is an aromatic, aliphatic or alicyclic carbon group, such as those comprising 2–10 carbon atoms. R may also contain substituents that improve the leaving group properties of X. See also further down. X may also be an intramolecular leaving group, i.e. a group that in addition to being attached to the 2-carbon of the fundamental carbonyl compound is also attached at some other position.
  R' and R" are selected among hydrogen, alkyl, aryl and X. The alkyl group may be straight, branched or cyclic, for instance comprising 1–10 carbon atoms. The aryl group may be a phenyl group. These alkyl and aryl groups may contain substituents, for instance one or more groups that enhance the ability of the grouping X—(CR'R") to undergo nucleophilic substitutions at the central carbon atom (single underlining) and/or elimination over the bond between the 1- and 2-carbon after nucleophilic attack also at the carbonyl group. R''' may be selected among the same groups as R' and R". In addition R''' may be a group X—CR'R", i.e. the carbonyl compound of formula I may be more or less symmetrical around the carbonyl group. The only proviso with respect to selecting R''' among the same alternatives as R' and R" is that substituents in R''' primarily should enhance nucleophilic attack at the carbonyl carbon and/or elimination over either the bond between the 1- and 2-carbons and/or elimination over the C—OH bond formed after nucleophilic attack also at the carbonyl carbon.

In preferred 2-substituted carbonyl compounds of formula I, none of R', R" and R''' are equal to X.

In general terms, the groups R, R', R" and R''' may also contain one or more substituents that increase the water-solubility and/or enhance the anti-pathogenic activity of the compound of formula I. With respect to water solubility suitable groups are more or less polar and hydrophilic, e.g. hydroxy, poly and oligo lower alkoxy (for instance —$(OCH_2CH_2)_nOH$ where n is an integer>0, for instance $\leq 10$), —COOH/—COO$^-$, —$COOR_1$, —$CONR_2R_3$ etc. $R_1$, $R_2$ and $R_3$ are lower alkyl, such as $C_{1-5}$ alkyl.

In addition, R', R" and R''' may pair-wise form cyclic structures together with the carbon atom in the CR'R" group (for R' and R") or with two carbon atoms in the —(CR'R")$_n$C(=O)—group (for R' and R" or R" and R''').

Preferably, the compounds of Formula I are 2-substituted aldehydes, i.e., m=0 and R''' is hydrogen. Preferred 2-substituted aldehydes are haloacetaldehydes. Haloacetaldehydes show efficient pathogen-inactivating effects. The magnitude of the pathogen inactivating effect will depend on the substituent(s) (R', R", R''' and X), and the pathogen to be inactivated.

The term haloacetaldehydes as used herein refers to 2-substituted aldehydes having a halogen substituent at the 2 position, and includes: (i) monohalo-acetaldehydes substituted with any of the halogens; (ii) polyhalogenated acetaldehydes, and (iii) mixed polyhalogenated acetaldehydes. The term haloacetaldehyde also contemplates proforms of a haloacetaldehyde, as that term is defined elsewhere herein. By use of the term "lower alkyl" is meant those containing one to about five carbons.

Preferred haloacetaldehydes are monohaloacetaldehydes, such as fluoroacetaldehyde, chloroacetaldehyde, bromoacetaldehyde, and iodoacetaldehyde (i.e., X is halo with preference for chloro and bromo, and still more preference for iodo; and R' and R" are both hydrogen).

Haloacetaldehydes, particularly iodoacetaldehyde (IAA), are potent disinfecting agents that can be used effectively in the presence of biological materials. Further, IAA mimics the disinfectant properties of the aqueous effluent taken from iodinated ion exchange matrices. See U.S. patent application Ser. No. 09/159,460. Thus, singular members of the class of compounds of the present invention can be used effectively in place of an effluent mixture from an iodinated ion exchange chromatographic matrix.

Without wishing to be bound by any theory, we believe that the pathogen-inactivating effect of these 2-substituted carbonyl compounds is caused by their reaction with a key component of a pathogen. The relevant key components of the pathogen have two nucleophilic groups (Y and Y") which are located on a common atom or on two separate atoms that are adjacent to each other. Each of the nucleophilic groups (Y and Y") in the most important cases have an amino or an amido nitrogen and/or a nitrogen of an aromatic or of a non-aromatic ring system as their nucleophilic center. The relative location of Y and Y" in the key components of the pathogen, and of X and the carbonyl group in the pathogen-inactivating 2-substituted carbonyl compound will enable reactions in which a 5- or 6-membered ring is formed as the primary adduct. The reaction may be driven towards ring formation by a subsequent elimination. Water may, for instance, be eliminated over the 1,2-bond in the part of the adduct deriving from the pathogen inactivating carbonyl compound. This particularly holds for pathogen-inactivating carbonyl compounds in which there is hydrogen at the 2-carbon. Stabilization may also be accomplished in case the atom or atoms between Y and Y" are part of an aromatic ring. This kind of adduct formation has been suggested between haloacetaldehydes and certain bases in nucleic acids (e.g. adenine, cytosine and guanine). See Bory et al., Mutagenesis 9(5) (1994) 407–410 and Premaratne et al., Int. J. Biochem 25(11) (1993) 1669–1672.

The common activity of the compounds described above will also be found in the use of compounds that are easily transformed to the above-mentioned type of carbonyl compounds (also referred to herein as "proforms"). Thus, it is known that the kind of carbonyl compounds defined above may be hydrated by adding water over the carbonyl double bond, may form ortho esters, or may form acetals or hemiacetals, which may be single or oligomeric or polymeric, may form diesters in which two acyloxy groups replace the carbonyl oxygen etc. Among oligomeric forms of acetals, cyclic trimeric forms are of greatest interest.

The conversion of a proform to the corresponding carbonyl-containing compound can be effected by, e.g., changing temperature, pH, or by catalytic or enzymatic processes. For certain proforms, the conversion does not need any change in condition. A proform may exert a pathogen inactivating effect by itself or by being transformed to its base form, i.e., to a 2-substituted carbonyl compound. Particularly preferred compounds of the invention may be those that in aqueous solutions exist to more than 30% as a proform (mol/mol).

One aspect of the invention is a method for inactivating a pathogen of the above-mentioned type in a material containing a pathogen by mixing the material with a pathogen-inactivating effective amount of a C-2 substituted carbonyl compound as defined above or a proform thereof. A method variant of the present invention thus includes inactivating pathogens by mixing a pathogen infected material with an aqueous mixture comprising a pathogen-inactivating-effective amount of a haloacetaldehyde. A preferred embodiment of the method is that wherein the pathogen is a virus and said pathogen-inactivating-effective amount of the pathogen-inactivating carbonyl compound is that which achieves a level of viral kill of at least about 1.0 $Log_{10}$ in virus titer. More preferably, the method will achieve viral kill capacity of greater than about 4.0 $Log_{10}$ in virus titer.

A particular advantage of the methods of the invention is the utility in disinfecting materials comprising clinically significant constituents such as proteins. A preferred embodiment is a method for inactivating pathogens in a biological fluid comprising contacting said biological fluid with an aqueous mixture comprising a pathogen-inactivating-effective amount of a pathogen inactivating carbonyl compound as defined above, or a proform thereof.

The pathogenic effect will vary for the different 2-substituted carbonyl compounds defined above, and with respect to the intended use. Thus, one of skill in the art will appreciate that certain optimization may be necessary as between the various members of the present class of compounds, with due regard to the particular biological fluid, the clinically significant constituents sought, and the suspected pathogens requiring inactivation.

Viruses inactivated by the compounds, compositions, and methods of the present invention are enveloped and non-enveloped viruses. The viral genomes consist of one or several molecules of DNA or RNA, which may be single stranded or double stranded, segmented, linear or circular. Viral genomic RNA may serve as mRNA after infection (RNA+) or as a template for transcription and replication (RNA-). Assembly of virions may take place in the cytoplasm, in the nucleus, via the plasma membrane etc. The viruses may belong to Reoviruses, Retroviruses, Parvoviruses, Poxviruses, Papovaviruses, Togaviruses, Picornaviruses, Herpesviruses, Rhabdoviruses, Filoviruses, Orthomyxoviruses, Hepadnaviruses, Adenoviruses, etc. Normal hosts include mammals, such as humans, simians, sheep, horses, cattle, rodents, etc.; avians; fishes; plants; bacteria, etc. Bacteriophages are included in the term virus.

Bacteria are also inactivated by compounds of the present invention. These include archaebacteria and eubacteria. The latter contains as its principal groups gliding bacteria, spirochetes, rigid bacteria and mycoplasmas. Rigid bacteria include actinomycetes and simple unicellular bacteria. The latter group consists of obligate intracellular parasites and free-living bacteria. Among the free-living variants there are (1) gram-positive bacteria in which group there are (a) cocci, (b) non-sporulating rods, (c) sporulating rods that can be further subdivided into obligate aerobes and obligate anaerobes; and (2) gram-negative bacteria in which there are (a) cocci, (b) non-enteric rods with spiral forms and straight rods, and (c) enteric rods with facultative anaerobes, obligate aerobes and obligate anaerobes. For specific bacteria species see further Medical Microbiology, (Brooks et al, eds., 19th ed. (1991), Prentice-Hall International, USA).

Pathogenic fungi, including pathogenic yeasts and molds, are also likely inactivated. Examples include Apergillus, Candida, Absidia, Mucor, Rhizopus, Cryptococcus, Hisoplasma, Blastomyces, Coccidiodes, Paracoccidiodes, Sporotrichosis, Chromoblastomycosis, Mycetoma, Microsporum, Trichophyton and Epidermophyton.

Other pathogens that are likely inactivated according to the invention may be found among the protozoa and algae. Prions, the infective agent of transmissible spongiform encephalopathies, and prion related proteins may also be inactivated by the compounds and methods of the present invention.

The compounds of the present invention are effectively compounded into disinfectant formulations or pharmaceutical compositions. Thus, another aspect of the invention is a pathogen-inactivating formulation or composition comprising one or more of the compounds of the present invention in combination with pharmaceutically acceptable vehicles, buffers, and excipients. The preferred vehicle is an aqueous diluent.

Various compounds of the present invention so far studied have demonstrated substantial anti-pathogenic capacity at concentrations as low as about 50 $\mu$M in the medium in which they are treated. Thus, it is contemplated that when looking at the whole group of pathogen-inactivating compounds as defined above, anti-pathogen capacity typically will be found in the concentration range of $10^{-9}$ M to about $10^{\circ}$ M, the optimal range varying between different pathogens, the material to be treated, anti-pathogenic compound used, desired time, temperature, etc. The preferred ranges at least for the monohaloacetaldehydes are believed to be found in the interval from at least about 50 $\mu$M to about 50 mM. Still greater concentrations may be appropriate depending on the active agent employed, particularly as against especially hardy or insidious pathogens.

Two or more pathogen-inactivating compounds may be present simultaneously in the composition/formulation.

As will be understood by those of skill in the art, the compositions of the present invention may further include buffers, preservatives, stabilizers, diluents, and excipients. For example, and as discussed more fully below, methods for disinfection of certain clinically significant constituents, including but not limited to Factor IX, benefit from the addition of calcium.

Although principally employed as an aqueous mixture, it is contemplated that the compositions of the present invention may be formulated as a powder, tablet, ointment, capsule, aerosol, and the like. The composition, or active constituents thereof, may be in dried form, e.g., a powder, lyophilized solid, or spray dried form. Such solid forms, may be formulated for reconstitution with various diluents, especially aqueous diluents.

In addition to conventional aqueous liquid carriers, other carriers or diluents may be used, particularly where the formulation is intended for non-therapeutic use. Such other diluents include water-insoluble liquids, and water-insoluble gels or solid matrixes. The active carbonyl compound may be incorporated into or attached to the carrier material.

In pharmaceutical compositions, the above-mentioned constituents shall be pharmaceutically acceptable. See generally REMINGTON'S PHARMACEUTICAL SCIENCES, (A. R. Gennaro et al., eds., $17^{th}$ ed. 1985).

The effective amount of a pathogen-inactivating compound depends on the particular 2-substituted carbonyl compound (or proform thereof) used, the pathogen to be inactivated, the material to be treated, etc. For most materials, the appropriate concentrations and other treatment parameters, can be determined by routine screening, for instance as outlined in the experimental part. Other treatment parameters include matching a specific carbonyl compound to a particular pathogen and/or to a material to be treated. We have found that active agents of the present invention (i.e., IAA hydrate) are effective at inactivating pathogens, e.g., porcine parvovirus (PPV), at concentrations as low as 50 $\mu$M; however, we expect that non-hydrated forms might be still more potent. Aqueous solutions of chloroacetaldehyde are effective at inactivating pathogens at CAA concentrations as low as about 1.0 mM. As above, this is not meant to suggest that these concentrations are the minimum effective quantities of active agent.

Screening as discussed above may be carried out by the actual user of the present invention or by some other individual having an interest in determining optimal conditions for the inventive method and in providing the information to the actual user.

As used herein, the term "a pathogen-inactivating-effective amount" of the agents of the present invention for inactivation of a pathogen, for instance a virus, means the amount sufficient to achieve a reduction in pathogen level, for instance in viral titer. Preferably this amount for a virus should give viral inactivation of at least about 1.0 $Log_{10}$ in virus titer. Preferred compounds and compositions of the present invention afford viral inactivation levels of greater than about 4.0 $Log_{10}$ in virus titer; and more preferably greater than 6.0 $Log_{10}$ in virus titer; and still more preferably greater than 10 $Log_{10}$ in virus titer.

Preferably, the "pathogen-inactivating-effective amount" of active agent for inactivation of a virus will be that of sufficient pathogen inactivating capacity as will inactivate the virus at a rate of at least about 0.2 $Log_{10}$/hour in virus titer. The methods of the present invention afford rates of viral inactivation of greater than 1.0 $Log_{10}$/hour in virus titer; and those rates are substantially linear over an incubation period of at least about 4 hours. Thus, depending on the length of the incubation period, it is contemplated that the methods of the present invention afford viral inactivation capacities of as much as 10 $Log_{10}$ in virus titer or more. Preferred methods and compositions of the present invention afford viral inactivation rates of greater than about 0.2 $Log_{10}$/hour in virus titer; and still more preferably, a pathogen inactivating capacity of greater than about 0.6 $Log_{10}$/hour in virus titer.

For other pathogens, analogous amounts giving reduction in pathogen levels apply. These levels may be expressed as reduction in number of $Log_{10}$ in pathogen levels.

The figures above refer to values obtained as demonstrated in the experimental part. Analogous model systems can be set up for non-viral pathogens with the measure of reduction in pathogen level being selected as known in the field for each particular class of pathogen.

Although the foregoing ranges are expressed in terms of viral kill, and viral kill is often demonstrated below with reference to PPV, it is expected that similar or greater levels of anti-pathogenic effect are achieved against other pathogens. PPV is one of the most rugged and hardy viral pathogens. Other viruses will be expected to be inactivated faster and more effectively at lower concentrations of active agent. Bacterial pathogens might be inactivated even more readily than viruses. Thus, although PPV is used here to demonstrate viral kill capacity, it is not meant to suggest that the pathogen inactivating species are effective against only one, or one class of, pathogen. Further, viral kill capacity against other, less hardy viruses and other pathogens, such as bacteria, would be expected to be substantially higher than the figures presented here meaning that the figures above apply in an analogous fashion to pathogens other than PPV.

The compositions of the present invention, when formulated as an aqueous composition is preferably pH adjusted to a pH value of about 3 to about 10, such as 5–10; preferably, the pH is adjusted to about 6 to about 8; and more preferably about 6.5 to about 7.5. Adjustment of pH will also be dictated by the proteins or clinically significant materials being disinfected. Thus, for example, biological fluids containing Factor VIII and Factor IX should not be treated at pH below 6.0, and is preferably maintained at a pH of about 6.0 to about 7.0; and more preferably about 6.2 to about 6.8. The pH shall be selected so that the pH in the medium in which pathogen-inactivation is taking place is non-denaturing for the material to be treated without being harmful to either the 2-substituted carbonyl compound used or the clinically significant components being disinfected. The pH ranges given for the composition apply also to the medium in which treatment is taking place.

The compositions of the present invention preferably incorporate pharmaceutically acceptable buffers. Preferred buffers are pharmaceutically acceptable acetate and phosphate buffers. Especially preferred are sodium or potassium phosphate buffers.

Additionally, one should avoid incorporating buffers, excipients, and/or other additives that include strong nucleophilic groups that inactivate the compounds of the present invention. Strong nucleophilic groups to be avoided in the compositions of the present invention include those containing amine, thiol and thiosulphate functionalities. Thus, for example, certain buffers, excipients, and additives containing such strong nucleophilic groups should be avoided in formulations of the present invention. Buffers and substances to be avoided include: triethylamine, diethylamine, 2-mercaptoethanol, ethanolamine, Tris, HEPES, MEPES, and compositions containing amino acids such as histidine and lysine. It follows that amines may be present as long as the pH is adjusted to a value where the major part of the amine is protonated, and that the negative impact may be acceptable for sterically hindered amines (for instance triethylamine, diethylamine etc) compared to monoalkylamine functionalities.

What has been said above about constituents in compositions and formulations in principle also applies to the medium in which pathogen-inactivation is taking place.

The pathogen-inactivating method of the present invention is preferably carried out at temperatures in which there is no significant competing degradation of the carbonyl compound, for instance hydrolysis. In case a biological material is treated the temperature should be selected to cause no irreversible heat denaturation. This means that for materials containing bioorganic compounds and/or clinically significant constituents that are heat-sensitive, the temperature is typically below 40° C., with an optimal effect typically in the interval 30° C.–40° C. These ranges apply in particular to haloacetaldehydes.

In case the material to be treated is heat-resistant, the inventive method may be carried out at elevated temperatures, for instance up to 80° C., providing the 2-substituted carbonyl compound and the conditions have been appropriately selected.

The time periods for contact between the carbonyl compound and the pathogen depends on the particular carbonyl compound used, material to be treated, pathogen etc. Typically at least about an hour is needed. In case of medical treatments, for instance topical, the treatment may be repeated.

Residual amounts of the active agent might remain in the disinfected material or biological fluid after inactivation of pathogens. It may prove desirable to remove such residual amounts of the active agent from the biological fluid or from the recovered clinically significant constituent. Depending on its physical and chemical properties, the carbonyl compound may be either destroyed or removed. Where the 2-substituted carbonyl compound is volatile, the carbonyl compound can be removed by evaporation, for instance simultaneously with a drying process utilizing freeze- or spray-drying.

Alternatively, the active agent might be removed or isolated from the biological fluid by conventional chemical separations methods employed with biological materials, particularly: (i) dialysis or diafiltration; or (ii) chromatographic separations methods.

Finally, the active agent itself might be destroyed. For example, addition of nucleophiles such as hydroxide ions (pH-increase), amines, thiols, thiosulfates, etc may be added, with due care taken to avoid destruction or denaturation of the clinically significant components of the disinfected material. Where the disinfected material is to be used in vivo it will also be important not to add or to create toxic components therein.

The compounds and compositions of the present invention are useful in non-therapeutic treatments. By non-therapeutic treatments is meant, e.g., treatment of therapeutically useful biological fluids in order to prevent the spread of disease. The term is thus employed to refer to treatment of blood, plasma, and blood products containing clinically significant constituents such as proteins and the like. As such, the term is distinguished from a therapeutic treatment of an individual host infected or otherwise at risk of infection from a pathogen. Most commonly, non-therapeutic treatments will be employed in biological fluids or other mixtures that are aqueous.

The compounds and compositions may also be used in a therapeutic context, i.e., treating a patient already infected or at risk for being infected by a pathogen, wherein the pathogen is sensitive to the pathogen-inactivating compounds defined above. Potentially the treatment involves external topical application/administration as well as internal or systemic administration to the patient. Other therapeutic concepts are ex vivo treatment of various body organs and other tissues that are to be transplanted, including also extracorporeal treatments. The patient is primarily of vertebrate origin such as a mammal, including humans.

In still other preferred modes of the methods and compositions of the present invention, the active carbonyl compound (a) has not been obtained from an iodine-loaded carrier material, such as an iodinated ion exchange matrix material and/or (b) is substantially free of molecular iodine, iodide ions, triiodide ions, hypoiodous acid (HOI), hypoiodite (IO$^-$) and/or other purely inorganic iodine compounds that are byproducts from a manufacturing method according to (a). Compare further WO 9516511; WO 9748422; WO 9748482; and U.S. patent application Ser. No. 09/159,460.

Other aspects of the invention are (a) the carbonyl compounds discussed above for the therapeutic inactivation of pathogens and (b) the use of the carbonyl compounds for manufacture of a pharmaceutical composition to be used for the therapeutic inactivation of pathogens.

Still other aspects of the invention are illustrated in the claims attached.

The invention will now be illustrated with non-limiting examples. The invention is further defined in the attached claims.

Experimental

EXAMPLE 1.

Synthesis, Purification and Analyses of Iodoacetaldehyde (IAA)

A. Synthesis of IAA

Iodoacetaldehyde (IAA) was synthesized by the method of Glinsky G, Z Chem, 618 (1868) with substantial modifications. Chloroacetaldehyde, 2 mmole (45% aqueous solution, 6.9 M) was diluted to 0.29 M in 7 mL acetone. Sodium iodide (2 mmole) was added with mixing and the mixture was incubated for 18 h at room temperature. The reaction mixture was filtered to remove solid material, and 5.5 mL of the filtered solution was diluted 5-fold with water. To remove unreacted iodide and iodine, the diluted sample was passed at 5 mL/min through an 8.5 mL column of DEAE-Sephadex (Amersham Pharmacia Biotech AB, Uppsala, Sweden) swelled in 20% acetone. The first 7 mL of effluent was discarded and the rest collected. The column was washed with 5 mL of 20% acetone and the effluent was added to the collected pool.

B. Purification of Synthesized IAA

Purification of synthesized samples was performed by reverse phase chromatography (RPC) on Source 15 RPC matrix (Amersham Pharmacia biotech AB, Uppsala, Sweden) packed in a 4.6×150 mm column (2.4 mL resin). The mobile phase consisted of Buffer A: 0.1% trifluoracetic acid (TFA) and Buffer B: 70% acetonitrile (CH$_3$CH). The column was equilibrated in 5% Buffer B and 95% Buffer A. A linear gradient from 5% B to 100% B was developed in 10 column volumes. Sample volume of 0.5 mL was applied per run. For five repeated runs, the fraction eluting between 20–29% CH$_3$CN was pooled (fraction 5 in the chromatogram) to get enough material for testing. Purity was determined by GC-MS and NMR. GC-MS (solid phase micro extracted sample) showed a very pure peak at 170 Daltons with virtually no trace of any contaminating compounds (iodoacetone, chloroacetaldehyde). NMR studies confirmed high purity, but traces of acetaldehyde were detected. The concentration of IAA in the pool from the RPC column was estimated to be 1.8 mM by NMR.

C. Determination of relative amount and concentration of IAA and its hydrated form by NMR One-dimensional $^1$H-NMR spectra were recorded on a Bruker DRX 500 spectrometer at 40° C. The signal for TSP was used as internal reference ($\delta_H$=0.0 ppm). A sample was prepared by adding 50 μl of the solution purified by reverse phase chromatography (RPC) to 650 μl D$_2$O and subsequently transferring the diluted sample to a 5 mm NMR tube. For the quantitative measurement, a solution of Sodium Trimethyl Silyl Propionic acid (TSP, 0.991 mg/ml) was prepared; and 10 µl of that solution was added to the sample. By comparing the integral of the methyl groups in TSP with the integral of the $CH_2$-group in hydrated IAA, an estimate of the IAA concentration in the sample could be made. Iodoacetaldehyde is in equilibrium with its hydrated form in a water solution. An estimate based on NMR is that the hydrated form accounts for approximately 90% of the sample, and the aldehyde form approximately 10%. This equilibrium should be taken into account when calculating concentration of IAA in aqueous media.

EXAMPLE 2
Virus Inactivation Capacity of Iodoacetaldehyde (IAA) in the Presence and Absence of Human Plasma Immunoglobulin This experiment was designed to determine the concentration dependence of IAA for inactivation of porcine parvovirus, a rugged nonenveloped virus, and to compare the results of IAA in buffer and in 5% immunoglobulin solution.

RPC-purified IAA was diluted to the desired µM concentrations in water or in 5% IgG solution (>98% pure, KABI, Stockholm, Sweden), and the pH was adjusted to ~5.00 with 0.4 M sodium phosphate. Virus was spiked into each sample at a ratio of 1:10. To 4.5 ml of each sample in 50 ml Falcon tubes, 0.5 ml of PPV stock was added. The virus-spiked solutions were incubated at 37° C. for 4 hours on a shaking water bath, and were immediately placed on ice to terminate any heat dependent reaction. The samples were then gel filtered through sterile PD 10 columns containing Sephadex G-25 (Amersham Pharmacia Biotech Uppsala, Sweden) equilibrated with 25 ml of cell culture medium. A sample (2 ml) was layered onto the column and the fall-through was discarded. Then 3.2 ml cell culture medium (3.2 ml) was added to the column and the first 0.5 mL of eluate was discarded. The remaining eluate was collected for viral assay. The resulting diluting factor was 1.48.

Materials for viral assays were as follows. Porcine parvovirus, strain PPV 893/76 was obtained in cell culture supernatant (Department of Vaccine Research, SVA, Uppsala, Sweden) in Eagle's MEM (EMEM) with non-essential amino acids. The cell supernatant was clarified by low speed centrifugation and filtered through 0.45 µm and 0.2 µm filters before storing at −70° C. in aliquots. The target cells for titration of PPV were porcine kidney cell line PK 15 (ATCC CCL-33). The cells were cultivated according to conventional cell culture procedures in EMEM with non-essential amino acids (SVA, Uppsala, Sweden), supplemented with 120 µg/ml of penicillin G, 100 µg/ml of streptomycin sulfate and 5% fetal calf serum. Cells were seeded in 96 well microtiter plates (Nunc).

Viral assays were performed by a $TCID_{50}$ method. The original virus stock (positive control sample) and the test samples were serially diluted ten-fold in cell culture medium shortly after sampling. Aliquots (50 µl) of each dilution were added to eight wells of the 96-well microtiter plates. Test samples were titrated $10^{-1}$ to $10^{-4}$, and the virus control was titrated $10^{-1}$ to $10^{-8}$. After incubation for 7 days at 37° C. in a humidified atmosphere of 5% $CO_2$, the cells were rinsed in physiological saline and fixed in 80% acetone for 30 minutes at −20° C., after which the fixation fluid was removed and the plates were dried at 37° C.

Figure 1:
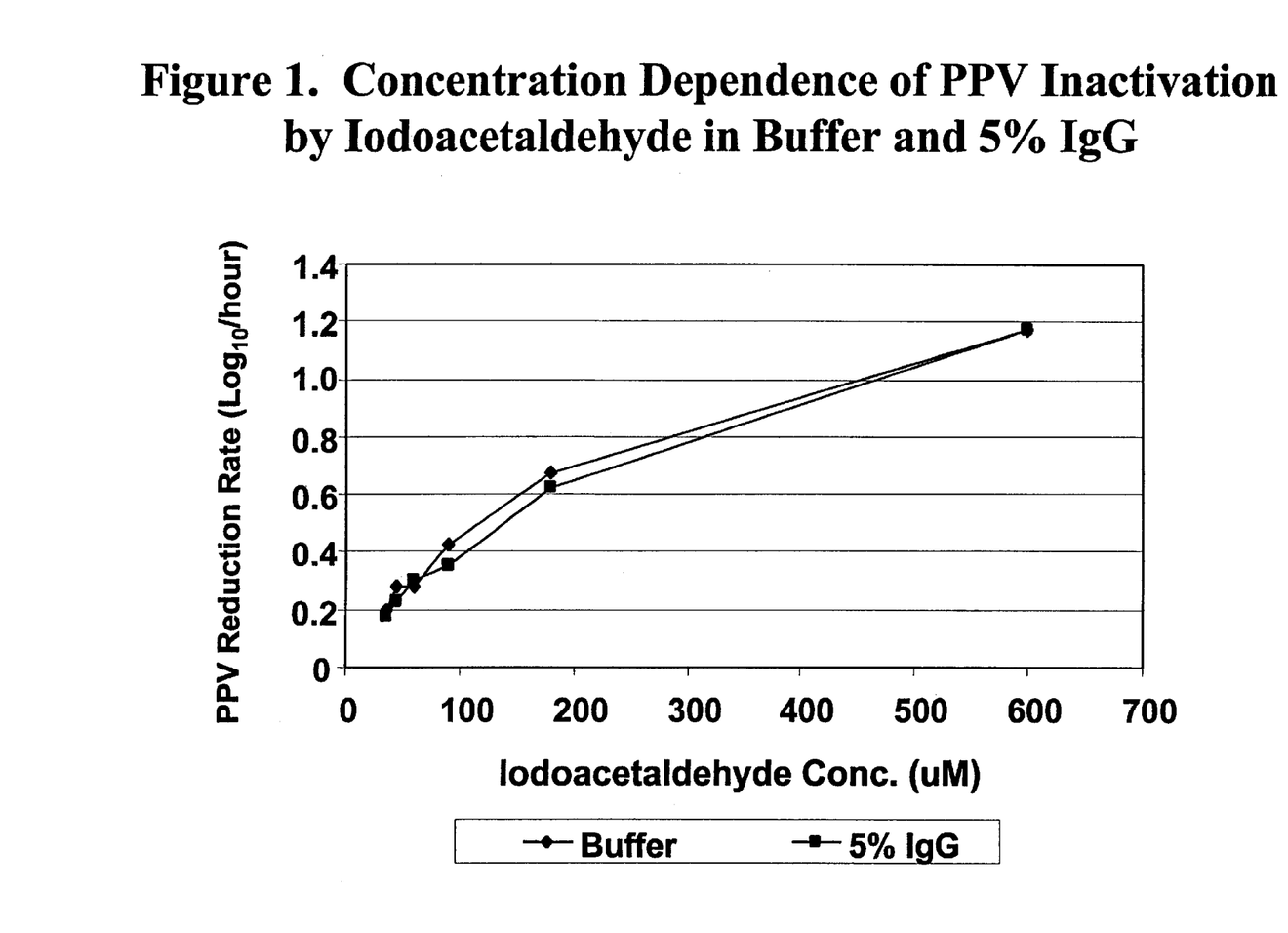
FIG. 1 is a graph illustrating the concentration dependence of porcine parvovirus (PPV) inactivation by iodoacetaldehyde in buffer and 5% IgG, and reports the PPV reduction in units of $Log_{10}$/hour at 37° C.
Figure 2:
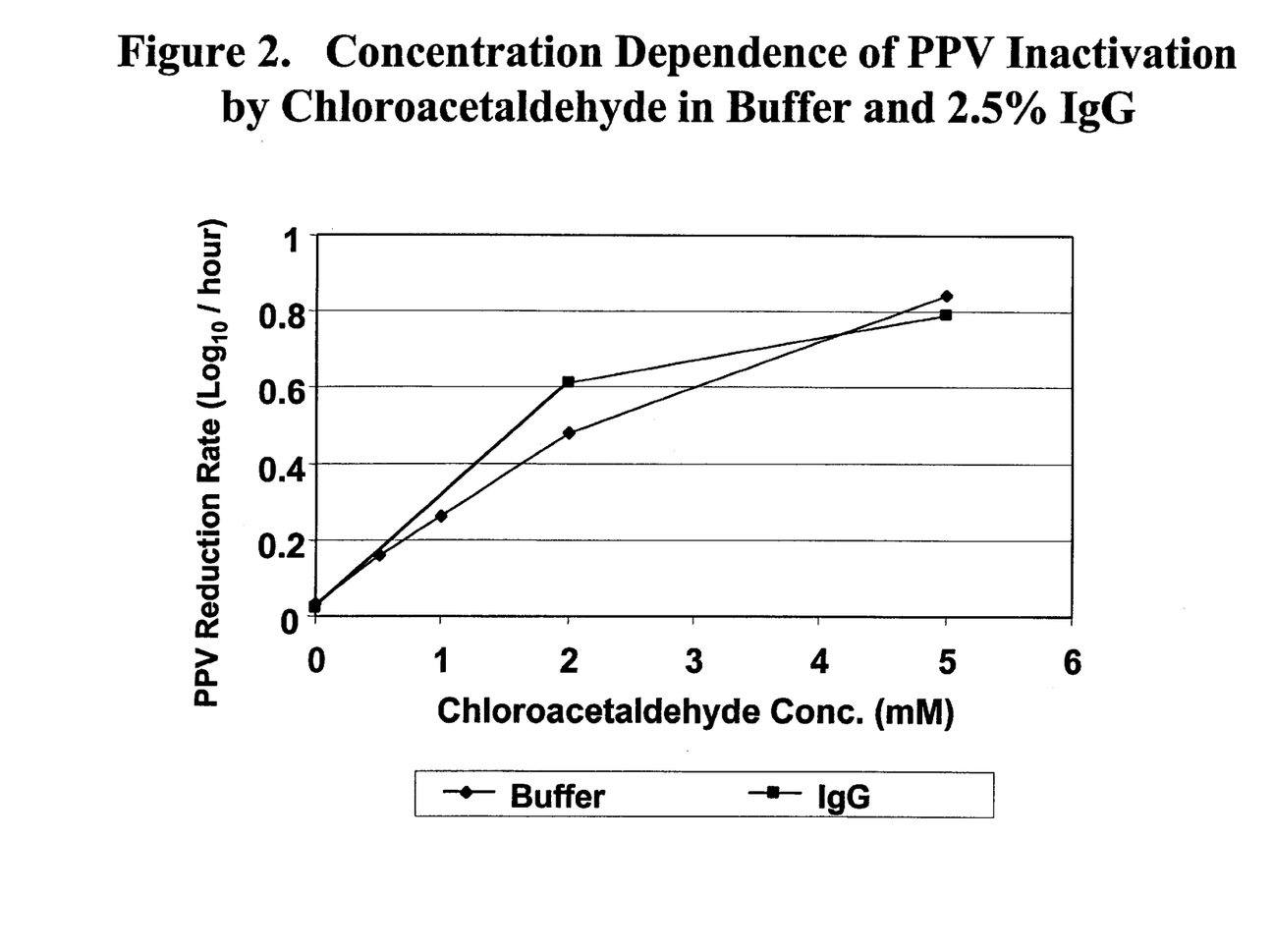
FIG. 2 is a graph illustrating the concentration dependence of porcine parvovirus (PPV) inactivation by chloroacetaldehyde in buffer and 2.5% IgG, and reports the PPV reduction in units of $Log_{10}$/hour.

Virus infected cells were visualized by an immunoperoxidase method (Jensen M. H., ACTA VET. SCAND. 22 (1981) 85–98; Meyling A., RECENT ADVANCES IN VIRUS DIAGNOSTICS, McNutly and McFerran, eds. (1984) 37–46; Saunders G. C., Am. J. VET. RES. 38 (1977) 21–25). A dilution of mouse anti-PPV monoclonal antibody, α-PPV 5B 82902 (Svanova Biotech, SVA, Uppsala, Sweden), was added to each well and the plates were incubated for 1 hour at 37° C. The cells were then washed twice for five minutes with wash fluid and once with physiological saline. Peroxidase-conjugated rabbit anti-mouse IgG P 2060 (Dakopatts, Denmark) was added to the cells. The plates were incubated for 1 hour at 37° C. and then again washed as above. After pH-adjustment with sodium acetate buffer, the plates were incubated for 20 minutes at 30° C. with peroxidase substrate, which imparted a reddish-brown color to the nuclei and cytoplasm of PPV infected cells. Wells with viral foci were counted using an inverted microscope and the tissue culture infectious dose giving a 50% end point ($TCID_{50}$) was calculated for each sample. Virus reduction factors (R) were calculated from the titer at 4 hours incubation using the formula:

$$10^R = (v' \times 10^{a'})/(v'' \times 10^{a''})$$

where
  v'=starting volume=5 mL
  $10^{a'}$=starting titer=positive control titer divided by 10.
  v''=final volume=5 mL
  $10^{a''}$=final titer The PPV reduction factors ($\log_{10}$/4 hours) for 4-hour incubation of 37° C. with several concentrations of IAA in buffer or in 5% immunoglobulin solution are shown in the Table 1 and in FIGS. 1 and 2.

TABLE 1

| Diluent | IAA concentration* (µM) | pH | PPV Reduction Factor $\log_{10}$/4 hours |
|---|---|---|---|
| Buffer | 600 | 4.84 | ≧4.7 |
|  | 180 | 4.93 | 2.7 |
|  | 90 | 4.95 | 1.7 |
|  | 60 | 4.96 | 1.1 |
|  | 45 | 4.96 | 1.1 |
|  | 36 | 4.96 | 0.8 |
| 5% IgG | 600 | 4.56 | ≧4.7 |
|  | 180 | 4.61 | 2.5 |
|  | 90 | 4.62 | 1.4 |
|  | 60 | 4.64 | 1.2 |
|  | 45 | 4.64 | 0.9 |
|  | 36 | 4.64 | ≦0.7 |

*Hydrated form

At each IAA concentration, virus reduction factors were equal in the presence or absence of protein. The inactivation rate was dependent on IAA concentration in a nearly linear fashion up to 200 µM IAA (FIGS. 1 and 2). The pH values for all samples were similar (mean=4.78±0.17). Control experiments showed that PPV was not inactivated by the residual solvent contaminants acquired through RPC purification of IAA (not shown).

This example illustrates the potent virus inactivation capacity of iodoacetaldehyde. At 180–600 micromolar concentrations, IAA rapidly inactivated porcine parvovirus, one of the most rugged viruses of the non-enveloped virus class. Inactivation of less hardy viruses by IAA would be expected to equal or exceed the inactivation of PPV. The finding of equal PPV inactivation rates in the absence and presence of IgG is of importance. At 5% protein, the IgG molar concentration was approximately 320 µM. The highest concentration of IAA (600 µM) was less than twice the protein molarity, and the second-highest IAA concentration (180 µM) was only about one-half the protein molarity. Any reaction of IAA with even a small fraction of the protein molecules would consume a significant portion of the IAA and render it ineffective for inactivation of virus. This is strong evidence that the IAA is not consumed by, and does not react with, the protein. It also shows that the virus inactivation process is not sensitive to the protein environment, and is therefore a robust process that should give consistent, reproducible results in the treatment of plasma proteins.

EXAMPLE 3

Inactivation of Porcine Parvovirus by Chloroacetaldehyde (CAA) in the Presence and Absence of Human Plasma Immunoglobulin This experiment was designed to determine the concentration dependence of parvovirus inactivation by CAA, and to compare the results of CAA in buffer and in 2.5% immunoglobulin solution.

An aqueous solution of chloroacetaldehyde (Aldrich Chemical, Milwaukee, Wis., Product 31,727-6, Lot KS02106MR, 50% in water) was diluted to the desired mM concentrations (0.5, 1, 2 and 5 mM) in 0.05 M sodium acetate buffer, pH 5.5. The 2 mM and 5 mM CAA samples were also prepared in 2.5% IgG solution, buffered at pH 5.5 with sodium acetate. Positive hold controls contained 0.05 M sodium acetate buffer, pH 5.5, or acetate-buffered 2.5% IgG without CAA. Positive controls and test samples were spiked 1:40 with porcine parvovirus (ATCC VR-742, PPV strain NADL-2). Aliquots were removed for immediate viral assay and the remaining samples were incubated at 37° C. for 4, 7 and 22.5 hours and then assayed to determine viral titers.

Viral assays were performed by the $TCID_{50}$ method as described by Miekka et al, HEMOPHILIA 4, 401–408 (1998). Target porcine kidney cells, PK-13 (ATCC CRC-6490), were seeded into 96-well microtiter plates and grown to 50–70% confluence. Five-fold serial dilutions (200 μL) of samples were prepared in cell culture medium and added to four wells each. Plates were incubated for 7 days at 37° C. in humidified 5% carbon dioxide. Cell layers were analyzed for cytopathic effect, and $\log_{10}$ viral titers were calculated by the method of Kärber,ARCH. Exp. PATHOL. PHARMAKOL., 162, 480–483 (1931). The average PPV reduction rate ($\log_{10}$/hour) was computed by regression analysis of the viral titers at each of the time points tested. Viral titers that had decreased to the assay limit were excluded from this calculation.

The average rate of PPV reduction ($\log_{10}$/hour) during 37° C. incubation with CAA in buffer and in 2.5% immunoglobulin solution are shown in Table 2.

TABLE 2

| Diluent | CAA concentration mM* | pH | Average PPV Reduction Log$_{10}$/hour |
|---|---|---|---|
| Buffer | 5 | 5.56 | ≧0.84 |
|  | 2 | 5.50 | 0.48 |
|  | 1 | 5.40 | 0.26 |
|  | 0.5 | 5.40 | 0.16 |
|  | 0 | 5.40 | 0.03 |
| 2.5% IgG | 5 | 5.50 | ≧0.79 |
|  | 2 | 5.36 | 0.61 |
|  | 0 | 5.40 | 0.02 |

*Total Concentration (hydrated + non-hydrated)

Figure 3:
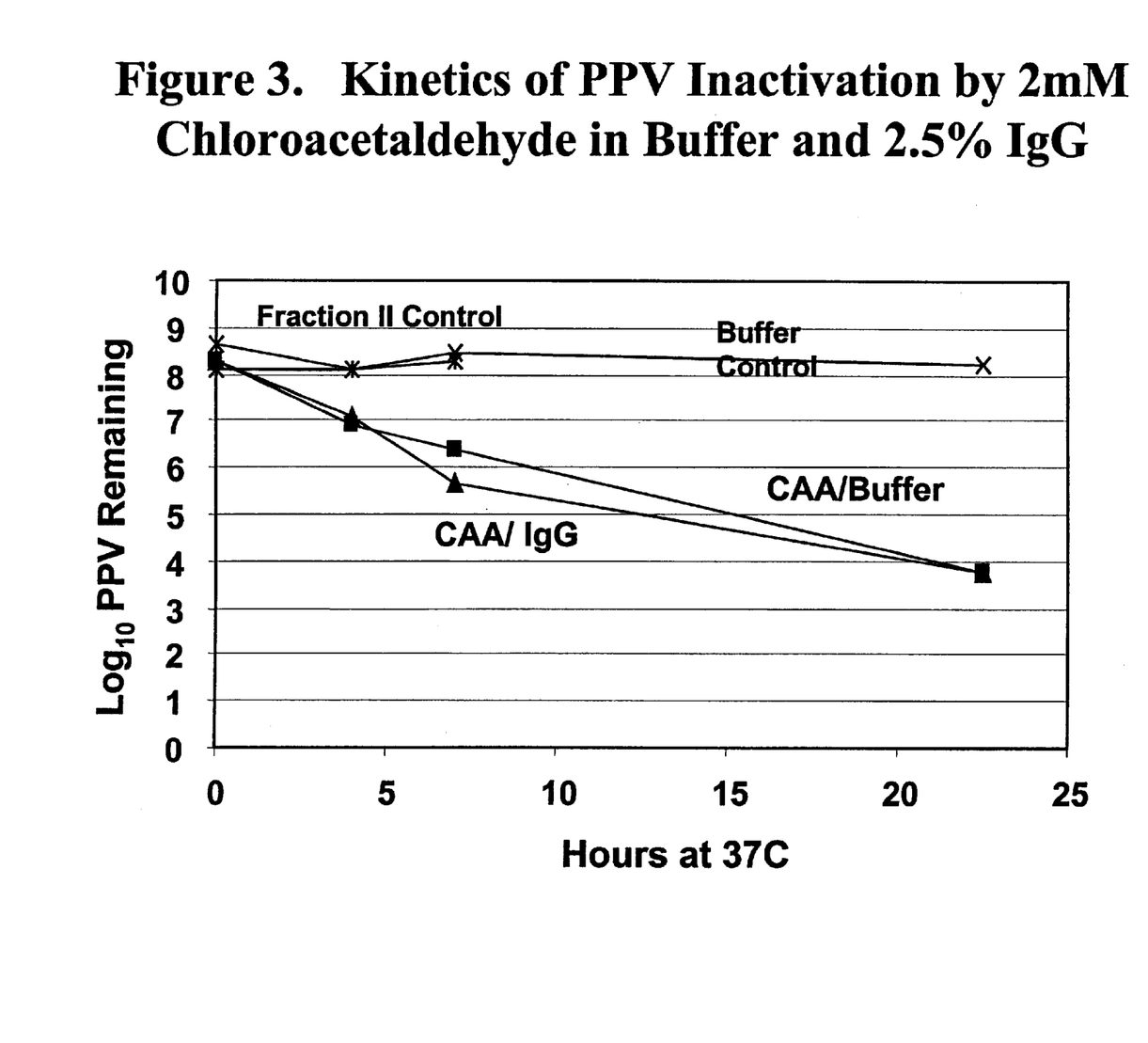
FIG. 3 is a graph illustrating the kinetics of PPV inactivation by 2 mM chloroacetaldehyde in buffer and 2.5% IgG.
Figure 4:
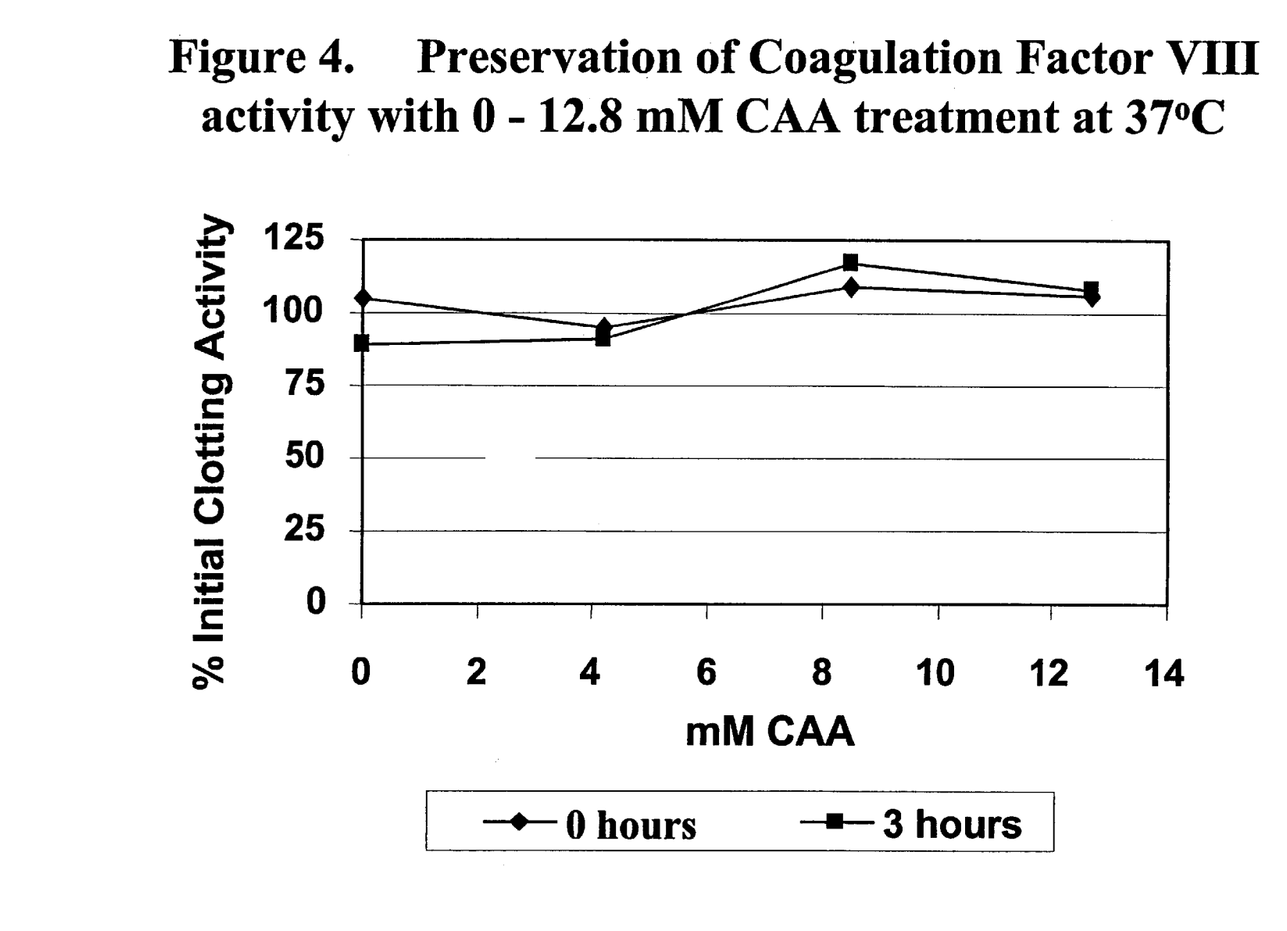
FIG. 4 is a graph illustrating the preservation of coagulation Factor VIII activity with 0–12.8 mM CAA treatment at 37° C.

The inactivation rate was dependent on CAA concentration in a nearly linear fashion up to 2 mM CAA (FIG. 3). At 5 mM CAA the titer reached the detection limit of the assay at 4 hours (rate≧0.84 $\log_{10}$/hour). Incubation times shorter than 4 hours would be required to determine the exact inactivation rate. In the presence of 2.5% IgG, PPV was inactivated at a rate similar to the rate in buffer alone. The kinetics of the PPV inactivation by CAA is illustrated in FIG. 4. With 2 mM CAA, PPV titers continuously decreased during 23 hours of 37° C. incubation, attaining equal inactivation rates in buffer and in 2.5% IgG. Hold control titers did not decrease throughout the incubation period.

This example illustrates that CAA is capable of inactivating PPV, a hardy nonenveloped virus. Inactivation by CAA is not inhibited by the presence of IgG, suggesting that CAA does not react with, and is not consumed by, the protein. This is consistent with the similar results obtained with IAA (EXAMPLE 2) in the absence and presence of 5% IgG. However, CAA is much less potent than IAA. At 180 μM concentration, IAA gave approximately the same rate (0.6 $\log_{10}$/hour) as 2 mM CAA. Thus IAA is over 10 times more potent than CAA under these conditions.

EXAMPLE 4

Inactivation of a Lipid-Enveloped Virus by Haloacetaldehydes

The purpose of this experiment was to test the ability of haloacetaldehydes and Iodine/Sepharose column effluents to inactivate a model virus of the lipid-enveloped class.

The test virus was pseudorabies virus (PRV), frequently used as a model for lipid-enveloped viruses. The following solutions were prepared: 2 mM and 5 mM chloroacetaldehyde (CAA); an impure IAA preparation, synthesized by a modification of the method of Chartaud, ANN CHIM. PHYS 16: 147 (1889) diluted to contain <1 mM IAA; and a sample of Iodine/Sepharose aqueous column effluent (EXAMPLE 8) diluted 1:1 with water. All samples were buffered at pH 5.5 with 0.02 M sodium acetate. The positive hold control was 0.02 M sodium acetate buffer without additives. The test samples and hold control were spiked 1:10 by mixing 0.9 mL of sample with 0.1 mL stock suspension of PRV (ATCC VR-135), incubated for 4 hours at 37° C. and then diluted and tested in 96-well microtiter plates by the $TCID_{50}$ method. Target cells were Vero cells (ATCC CCL-81). All other aspects of cell propagation and virus assay were as described for PPV in EXAMPLE 3.

Results of pseudorabies inactivation are presented as reduction factor ($\log_{10}$ reduction in 4 hours) and as average inactivation rate ($\log_{10}$/hour). All haloacetaldehyde samples inactivated PRV as effectively as the same samples inactivated PPV (EXAMPLES 2 & 3, or not shown).

TABLE 3

| | | Pseudorabies Virus Results | |
|---|---|---|---|
| Sample | Concentration* | Reduction Factor ($\log_{10}$/4 hours) | Av. rate ($\log_{10}$/hour) |
| Bench Control | 0 | 0 | 0 |
| CAA | 2 mM | 2.10 | 0.66 |
| CAA | 5 mM | ≧3.15 | ≧0.79 |
| Impure IAA | <1 mM | 3.47 | 1.09 |
| Column Effluent | Diluted 1:1 | 3.85 | 0.96 |

*Total Concentration (hydrated + non-hydrated)

These results show that CAA is able to inactivate model viruses of the lipid enveloped class (PRV) as well as of the non-enveloped class (PPV). The rate of inactivation by CAA was similar for PRV and for PPV (compare these results with EXAMPLE 3). PPV is a small non-enveloped virus (Parvovirus family) with single-stranded DNA genome, whereas PRV is a large lipid-enveloped virus (Herpes virus family) with double-stranded DNA genome. The vastly different surface properties of the two viruses (lipid envelope v. protein capsid, different surface antigens) argue for an inactivation mechanism based on reaction with common viral structures (e.g, modification of the nucleic acid genome).

EXAMPLE 5
Preservation of Factor VIII Activity with Chloroacetaldehyde (CAA) Treatment This experiment was designed to assess the effect of haloacetaldehydes on the clotting activity of immunoaffinity-purified human coagulation Factor VIII (CFVIII, antihemophilic Factor).

The CFVIII product tested was 'Antihemophilic Factor, Human, Method M, Solvent and Detergent Treated' (American Red Cross). A stock solution of 100 mM CAA in water was neutralized to pH 7.0 and was added to give final CAA concentrations of 4.2 mM, 8.5 mM and 12.7 mM, and a final CFVIII concentration of 100 units/mL. The samples were incubated for 3 hours at 37° C., and were assayed for CFVIII clotting activity by the one-stage activated partial thromboplastin time (APTT) method of Denson (in Biggs R, HUMAN BLOOD COAGULATION HAEMOSTASIS AND THROMBOSIS, 1972, Oxford, Blackwell Scientific, 614–616).

Figure 5:
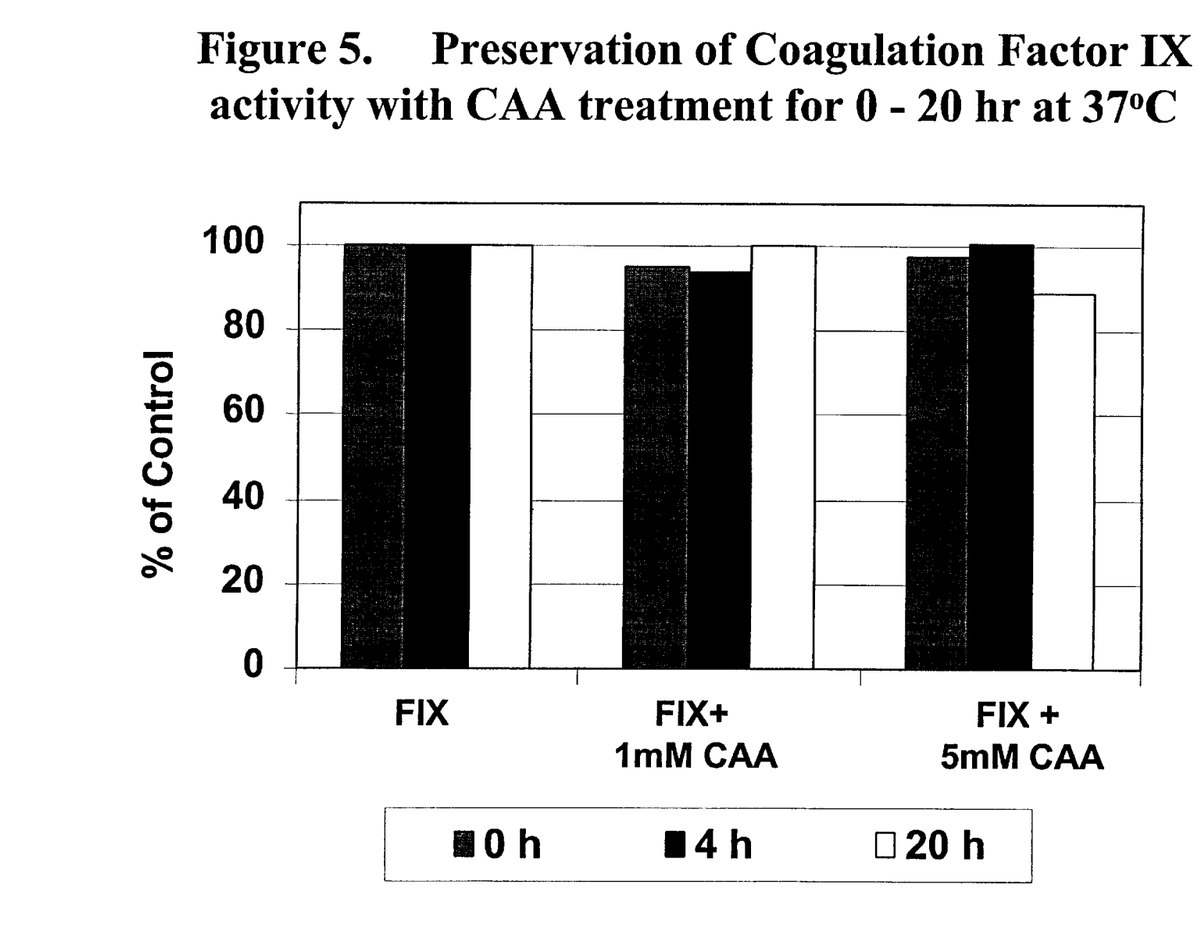
FIG. 5 is a graph illustrating the preservation of coagulation Factor IX activity with CAA treatment at 0 hours, 4 hours, and 20 hours, all at 37° C.

The retention of Factor VIII clotting activity after 3-hour incubation with varied concentrations of CAA in two experiments is shown in the table and in FIG. 5. Factor VIII activity was not diminished by treatment with CAA. Recovery was essentially 100% at 8.5 and 12.7 mM CAA, the highest concentrations tested.

TABLE 4

| Experiment # | CAA Concentration (mM)* | FVIII u/mL after 37° C. incubation 0 hour | FVIII u/mL after 37° C. incubation 3 hours | % Recovery of FVIII clotting activity |
|---|---|---|---|---|
| 1 | 0 | 105 | 89 | 84.8 |
|   | 4.2 | 95 | 91 | 95.8 |
|   | 8.5 | 109 | 117 | 107.3 |
|   | 12.7 | 106 | 108 | 101.9 |
| 2 | 0 | 115 | 114 | 99.1 |
|   | 4.2 | 121 | 186 | 153.7 |
|   | 8.5 | 88 | 105 | 119.3 |
|   | 12.7 | 89 | 91 | 102.2 |

*Total Concentration (hydrated + non-hydrated)

The recovery of Factor VIII activity was nearly 100% after 3 hour incubation with up to 12.7 mM CAA. Incubation for 4 hours with 5 mM CAA inactivates ≧3.2 –4 $\log_{10}$ of porcine parvovirus and ≧3.2 $\log_{10}$ of pseudorabies virus, considered to be hardy model viruses of the non-enveloped and lipid enveloped classes, respectively. Factor VIII, an important therapeutic plasma product, is known to be a labile clotting factor. Retention of the activity of this Factor is further evidence for the benign nature of haloacetaldehydes with regard to human plasma proteins.

EXAMPLE 6
Inactivation of PPV by Chloroacetaldehyde in the Presence of Factor VIII This experiment tested the ability of CAA to inactivate porcine parvovirus (PPV) in the presence of immunoaffinity-purified human coagulation Factor VIII (CF VIII).

A stock solution of 100 mM CAA in water was neutralized to pH 7.0 and was added to CFVIII to give final CAA concentrations of 3 mM and 6 mM and final CFVIII concentration of 100 clotting units/mL. All samples were buffered at pH 5.5 with 0.02 M sodium acetate. PPV was spiked into the samples at 1:40 ratio. The samples were incubated for 4 hours at 37° C. The positive hold controls were acetate buffer or Factor VIII, spiked with PPV and incubated 4 hours at 37° C. Viral assays and cell culture techniques were performed as described in EXAMPLE 3. Viral reduction factors were calculated as the difference between the $\log_{10}$ titers of the non-incubated and 4-hour incubated samples.

Inactivation of PPV by CAA with and without Factor VIII is shown below. At 4 hours of incubation, all of the samples reached the assay sensitivity limit. The stock titer of the PPV lot used was lower than previous experiments (~6.3 $\log_{10}$) and the assay limit due to reagent cytotoxicity was higher than usual (~4 $\log_{10}$). The reduction factors are therefore limited to ≧2 $\log_{10}$/4 hours or approximately ≧0.5 $\log_{10}$/hour. No difference was seen in the reaction rates with and without Factor VIII, indicating that neither Factor VIII nor its formulation components obliterated the viral inactivation ability of CAA.

TABLE 5

| Diluent | CAA Concentration (mM)* | Reduction Factor $\log_{10}$/4 hours | Average rate $\log_{10}$/hour |
|---|---|---|---|
| Buffer | 0 | 0 | 0 |
|  | 3 | ≧2.27 | ≧0.57 |
|  | 6 | ≧1.75 | ≧0.43 |
| Factor VIII (AHF-M) | 0 | 0 | 0 |
|  | 3 | ≧2.44 | ≧0.61 |
|  | 6 | ≧2.09 | ≧0.52 |

*Total Concentration (hydrated + non-hydrated)

Whereas EXAMPLE 5 showed that Factor VIII clotting activity was maintained in the presence of CAA, the results of this experiment show that PPV is effectively inactivated under similar conditions. The Factor VIII product is stabilized by human albumin, which is present in large excess over the Factor VIII concentration. The formulation also contains an amino acid (histidine), which might be expected to react with and consume the CAA, and therefore protect the virus from inactivation. This experiment indicates that this does not happen. The virus is inactivated under conditions similar to those in which the Factor VIII biological activity is preserved.

EXAMPLE 7
Preservation of Human Coagulation Factor IX Activity with CAA Treatment The purpose of this experiment was to determine the effect of haloacetaldehydes on the clotting activity of highly-purified human coagulation Factor IX, a labile plasma clotting factor.

Immunoaffinity-purified human coagulation Factor IX (CFIX) at 60 clotting activity units/mL was equilibrated in 0.05 M sodium acetate buffer, pH 6.2 containing 0.1 M sodium chloride and 0.01 M calcium chloride. Chloroacetaldehyde (Aldrich 31,727-6) was added at final CAA concentrations of 1 and 5 mM. Aliquots of each mixture were incubated at 37° C. for 0, 4 and 20 hours. CFIX clotting activity was assayed by the one-stage activated partial thromboplastin time (APTT) method of Denson (in Biggs R, HUMAN BLOOD COAGULATION HAEMOSTASIS AND THROMBOSIS, 1972, Oxford, Blackwell Scientific, 614–616).

The retention of Factor IX clotting activity after incubation without and with 1 mM and 5 mM chloroacetaldehyde (CAA) is shown in the table and in FIG. 6. That activity was not diminished by treatment with CAA. All activities were within the ±10% variation for replicate assays of Factor IX coagulation activity. Recovery of activity was 100.6% after 4-hour treatment with 5 mM CAA, conditions that inactivate ≥3.6 logs of porcine parvovirus.

TABLE 6

| Sample | % of initial clotting activity remaining after 37° C. incubation | | |
|---|---|---|---|
| | 0 hour | 4 hour | 20 hour |
| CFIX-M control | 100 | 100 | 100 |
| CFIX-M + 1 mM CAA | 95.2 | 93.9 | 100.3 |
| CFIX-M + 5 mM CAA | 97.7 | 100.6 | 89.1 |

After the above treatments, Factor IX was examined by several types of analysis. No degradation of the Factor IX molecule was observed with SDS-polyacrylamide gel electrophoresis (SDS-PAGE), and no mobility changes were detected with native PAGE or with isoelectric focusing (not shown). This indicates that the molecule is not degraded or aggregated, and that its charge and isoelectric point are unchanged.

Without added calcium ions, the recovery of Factor IX clotting activity was variable and was significantly less than that observed with calcium. After 20–22 hours of incubation with 5mM CAA in the absence of calcium, the mean recovery in three separate experiments was 42%±25% (not shown).

Factor IX is a labile clotting factor that is particularly sensitive to halogens. Treatment with molecular iodine or exposure to iodinated chromatographic matrices has been found to completely inactivate this Factor. The finding that this sensitive molecule is not inactivated or degraded by chloroacetaldehyde treatment indicates that this is a milder agent that is appropriate for treatment of labile proteins. Hardier protein molecules can also be expected to maintain their functional and physical properties without degradation upon exposure to haloacetaldehydes under conditions that inactivate viruses.

EXAMPLE 8
Correlation of the Effect of Various Treatments on the Antiviral Activity of Iodine/Sepharose Column Effluents and on Iodoacetaldehyde Present in such Effluents Column effluents of Iodine/Sepharose ($I_2$/S) were prepared by pumping one liter of deionized water through a 24 mL XK-16 column of Iodine/Sepharose resin and then immediately through a 24 mL XK-16 column of DEAE Sephadex A25. Iodine/Sepharose resin was prepared by contacting DEAE Sepharose Fast Flow with potassium iodide and iodine under conditions giving 23% iodine content. All resins and columns were products of Amersham Pharmacia Biotech (Uppsala, Sweden). For treatment at pH 12, the column effluent was supplemented with 0.02 M sodium acetate and 0.02 M sodium phosphate, and the pH was adjusted to 12 with sodium hydroxide. After 30 min at 22° C., the pH was adjusted to 5.5 by addition of hydrochloric acid. For the heating test, a 1.5 mL portion of column effluent was placed in a 1.5 mL Fisher centrifuge tube, tightly capped and incubated in a heating block at 80° C. for 20 hours. The effects of 2, 10 or 20 mM sodium thiosulfate were determined by adding a stock solution of thiosulfate to column effluent buffered at pH 5.5. Untreated and treated column effluent samples were tested for ability to inactivate porcine parvovirus using the method described in EXAMPLE 3. Similar treatments were applied to iodoacetaldehyde, synthesized and purified as described earlier. (EXAMPLE 1) The effect of each treatment was assessed by determining the content of the treated solution by GC-MS and NMR as discussed in EXAMPLE 1.

TABLE 7

| | PPV inactivation rate by | | Effect on Iodoacetaldehyde | |
|---|---|---|---|---|
| Treatment | Change | $-\log_{10}/4$ h | Change | Product(s) |
| No treatment | None | 3.2 | None | Iodoacetaldehyde |
| pH 12 (0.5 hour) | Decreased | 0.5 | Degraded | Hydroxyacetaldehyde |
| 80° C. (20 hours) | Decreased | 0.0 | Degraded | Hydroxyacetaldehyde |
| Sodium thiosulfate, 2–20 mM | Decreased | 0–0.2 | Degraded | Unknown product |

EXAMPLE 9
Correlation of the Effect of Dialysis Through Ultra Small-Pore Membranes (100 Dalton Molecular Weight Cut-Off) on the Antiviral Activity of Iodine/Sepharose Column Effluents and on Iodoacetaldehyde Present in Such Effluents Column effluents of Iodine/Sepharose ($I_2$S) were prepared as described in EXAMPLE 8. Samples (15 mL) of the effluent were dialyzed in cellulose acetate membranes having molecular weight cut-off of 100 Daltons (Spectropor). The dialysis regimens were a single dialysis against 15 mL of water or against three changes of 1 L of water. The ability of the starting sample, the dialyzed sample (inside the dialysis bag) and the dialysate (outside the bag) to inactivate porcine parvovirus were determined as described in EXAMPLE 3. The presence of iodoacetaldehyde in the starting material and the dialyzed samples were tested by GC-MS.

TABLE 8

| | PPV inactivation rate ($\log_{10}$/hour) | | |
|---|---|---|---|
| Dialysis (ultra-small pore membranes) | Starting effluent or inside the bag | Outside the bag | Iodoacetaldehyde (GC-MS result) |
| None | 0.79 | N/A | Present |
| Dialyzed once v. one volume water | 0.66 | 0.52 | Equal amounts of IAA inside and outside bag |
| Dialyzed 3X v. 66 volumes water | 0.08–0.27 | 0 | Not tested |

N/A = not applicable

What is claimed is:
1. A method for inactivating a pathogen in a material comprising:
 (a) providing a pathogen inactivating effective amount of a pathogen inactivating haloacetaldehyde; and
 (b) contacting the substituted carbonyl compound with the material under conditions causing inactivation of a pathogen and wherein the pathogen is a bacteria, virus or prion.
2. The method of claim 1, wherein the material is a biological fluid.
3. The method of claim 2, wherein contacting the haloacetaldehyde with a biological fluid occurs at about 30° to about 40° C.
4. The method of claim 2, wherein contacting the haloacetaldehyde with a biological fluid occurs over a period of at least about one hour.

5. The method of claim 2, wherein said pathogen-inactivating-effective amount is that which is capable of achieving viral inactivation of porcine parvovirus at levels of at least about 1.0 $Log_{10}$ in virus titer.

6. The method of claim 2, wherein the haloacetaldehyde and the biological fluid are maintained in contact for a period sufficient to achieve a viral inactivation level of porcine parvovirus of at least about 4.0 $Log_{10}$ in viral titer.

7. The method of claim 6, wherein the haloacetaldehyde is maintained in contact with the biological fluid at a temperature of about 30° to about 40° C.

8. The method of claim 2, wherein the pathogen inactivated is selected from the group consisting of viruses, bacteria, and combinations thereof.

9. A method for inactivating a pathogen in a material that is a biological fluid comprising:
    a. providing a pathogen inactivating effective amount of a haloacetaldehyde; and
    b. contacting the haloacetaldehyde with the biological fluid under conditions causing inactivation of a pathogen and wherein the pathogen is a bacteria, virus, or prion.

10. The method of claim 9, wherein the haloacetaldehyde is selected from the group consisting of chloroacetaldehyde, bromoacetaldehyde, and iodoacetaldehyde.

11. A method for disinfecting a clinically significant constituent in a biological fluid comprising contacting said biological fluid with an aqueous solution comprising a pathogen-inactivating-effective amount of a haloacetaldehyde, and recovering said clinically significant constituent from said biological fluid.

12. The method of claim 11, wherein said haloacetaldehyde comprises a C-2 substitution with a halogen selected from the group consisting of fluorine, chlorine, bromine, and iodine.

13. A method for disinfecting a material of clinical significance in a biological fluid comprising mixing said biological fluid with an aqueous mixture comprising a haloacetaldehyde, and incubating said mixture for a period sufficient to achieve viral inactivation levels of at least about 1.0 $Log_{10}$ in viral titer, and recovering said material of clinical significance.

14. The method of claim 13, wherein said haloacetaldehyde is selected from among fluoroacetaldehyde, chloroacetaldehyde, bromoacetaldehyde, and iodoacetaldehyde.

15. A method for disinfecting a material of clinical significance in a biological fluid comprising mixing said biological fluid with an aqueous mixture comprising iodoacetaldehyde, and incubating said mixture at about 30° to about 40° C., and recovering said material of clinical significance.

* * * * *

UNITED STATES PATENT AND TRADEMARK OFFICE
CERTIFICATE OF CORRECTION

PATENT NO.    : 6,436,344 B1  
DATED         : August 20, 2002  
INVENTOR(S)   : Miekka et al.

It is certified that error appears in the above-identified patent and that said Letters Patent is hereby corrected as shown below:

<u>Column 20,</u>
Line 56, change "substituted carbonyl compound" to -- haloacetaldehyde --.

Signed and Sealed this

Twenty-fourth Day of December, 2002

JAMES E. ROGAN
*Director of the United States Patent and Trademark Office*